US012706887B2

(12) United States Patent
Rapoport et al.

(10) Patent No.: US 12,706,887 B2
(45) Date of Patent: Aug. 11, 2026

(54) SECURE INTERFACES FOR NEURAL DEVICES

(71) Applicant: PRECISION NEUROSCIENCE CORPORATION, New York, NY (US)

(72) Inventors: Benjamin I. Rapoport, New York, NY (US); Mark Hettick, New York, NY (US); Craig H. Mermel, New York, NY (US); Manuel Monge, New York, NY (US); Mark Murphy, New York, NY (US); Daniel Trietsch, New York, NY (US)

(73) Assignee: PRECISION NEUROSCIENCE CORPORATION, New York, NY (US)

( * ) Notice: Subject to any disclaimer, the term of this patent is extended or adjusted under 35 U.S.C. 154(b) by 175 days.

(21) Appl. No.: 18/491,425

(22) Filed: Oct. 20, 2023

(65) Prior Publication Data

US 2024/0137348 A1 Apr. 25, 2024
US 2024/0236053 A9 Jul. 11, 2024

Related U.S. Application Data

(60) Provisional application No. 63/417,837, filed on Oct. 20, 2022.

(51) Int. Cl.

| | |
|---|---|
| ***G16H 40/67*** | (2018.01) |
| ***G06F 3/01*** | (2006.01) |
| ***H04L 9/40*** | (2022.01) |

(52) U.S. Cl.
CPC .......... *H04L 63/0428* (2013.01); *G06F 3/015* (2013.01); *G16H 40/67* (2018.01)

(58) Field of Classification Search
CPC ........... A61B 5/262; A61B 5/37; A61B 5/375; A61B 5/4836; A61B 5/6868; A61B 5/742;
(Continued)

(56) References Cited

U.S. PATENT DOCUMENTS 5,709,689 A 1/1998 Ferrante et al.
5,910,282 A 6/1999 Grozdanovski et al.
(Continued)

FOREIGN PATENT DOCUMENTS

AU 2020428944 A1 9/2022
AU 2024203319 A1 6/2024
(Continued)

OTHER PUBLICATIONS

International Preliminary Report on Patentability for Application No. PCT/US2022/78130, mailed on Apr. 25, 2024, 8 Pages.
(Continued)

*Primary Examiner* — George Manuel
(74) *Attorney, Agent, or Firm* — DLA PIPER LLP (US)

(57) ABSTRACT

A neural device system that can include a neural device configured to sense data associated with the subject or receive control input, an external device communicably coupled to the neural device, a storage medium communicable coupled to the external device, and one or more communications interfaces between the neural device, the external device, and the storage medium or components thereof, wherein the one or more communications interfaces comprise an encryption protocol.

10 Claims, 2 Drawing Sheets

(58) Field of Classification Search
CPC ........ G06F 3/015; G16H 10/60; G16H 20/30; G16H 20/40; G16H 40/63; G16H 40/67; H04L 63/0428
See application file for complete search history.

(56) References Cited

U.S. PATENT DOCUMENTS

| | | | |
|---|---|---|---|
| 6,831,991 | B2 | 12/2004 | Fridrich et al. |
| 7,389,144 | B1 | 6/2008 | Osorio et al. |
| 7,818,061 | B1 | 10/2010 | Palmer |
| 7,925,350 | B1 | 4/2011 | Palmer |
| 8,156,568 | B2 | 4/2012 | Gaitas et al. |
| 8,170,670 | B2 | 5/2012 | Stubbs et al. |
| 8,515,538 | B1 | 8/2013 | Osorio et al. |
| 8,516,568 | B2 | 8/2013 | Cohen |
| 8,546,568 | B2 | 10/2013 | Inouye et al. |
| 8,634,918 | B2 | 1/2014 | Chambers |
| 9,314,618 | B2 | 4/2016 | Imran et al. |
| 9,549,704 | B1 | 1/2017 | Buerger et al. |
| 10,135,849 | B2 | 11/2018 | Jha et al. |
| 10,265,081 | B2 | 4/2019 | Kennedy et al. |
| 10,363,420 | B2 | 7/2019 | Fried et al. |
| 11,013,923 | B1 | 5/2021 | Eubanks |
| 11,185,684 | B2 | 11/2021 | Cadwell |
| 11,640,204 | B2 | 5/2023 | Shenoy et al. |
| 12,008,987 | B2 | 6/2024 | Stavisky et al. |
| 2001/0054758 | A1 | 12/2001 | Isaak |
| 2003/0057506 | A1 | 3/2003 | Li et al. |
| 2005/0228421 | A1 | 10/2005 | Bilenski et al. |
| 2005/0261934 | A1 | 11/2005 | Thompson |
| 2006/0015153 | A1 | 1/2006 | Gliner et al. |
| 2006/0106431 | A1 | 5/2006 | Wyler et al. |
| 2006/0253163 | A1 | 11/2006 | Stubbs et al. |
| 2007/0005691 | A1 | 1/2007 | Pushparaj |
| 2007/0282398 | A1 | 12/2007 | Healey et al. |
| 2009/0082829 | A1 | 3/2009 | Panken et al. |
| 2009/0088763 | A1 | 4/2009 | Aram et al. |
| 2009/0132061 | A1 | 5/2009 | Stubbs et al. |
| 2009/0312817 | A1 | 12/2009 | Hogle et al. |
| 2011/0093052 | A1 | 4/2011 | Anderson et al. |
| 2011/0245835 | A1 | 10/2011 | Dodds et al. |
| 2012/0139269 | A1 | 6/2012 | Kouzuma |
| 2012/0277834 | A1 | 11/2012 | Mercanzini et al. |
| 2012/0302959 | A1 | 11/2012 | Fielder et al. |
| 2013/0014982 | A1 | 1/2013 | Segawa et al. |
| 2013/0108046 | A1 | 5/2013 | Andersen |
| 2013/0144362 | A1 | 6/2013 | Lee |
| 2013/0144365 | A1 | 6/2013 | Kipke et al. |
| 2013/0331856 | A1 | 12/2013 | Sage |
| 2014/0051960 | A1 | 2/2014 | Badower et al. |
| 2014/0100586 | A1 | 4/2014 | Pianca et al. |
| 2014/0185805 | A1 | 7/2014 | Andersen |
| 2014/0194944 | A1 | 7/2014 | Romanelli et al. |
| 2015/0111930 | A1 | 4/2015 | Aung-Din |
| 2015/0151114 | A1 | 6/2015 | Black et al. |
| 2015/0265180 | A1 | 9/2015 | Venkatesan et al. |
| 2015/0367122 | A1 | 12/2015 | Morshed et al. |
| 2016/0007874 | A1 | 1/2016 | Ma et al. |
| 2016/0120457 | A1 | 5/2016 | Wu et al. |
| 2016/0174863 | A1 | 6/2016 | Foerster et al. |
| 2016/0331994 | A1 | 11/2016 | Smith et al. |
| 2017/0001003 | A1 | 1/2017 | Pivonka et al. |
| 2017/0100580 | A1 | 4/2017 | Olson |
| 2017/0108926 | A1 | 4/2017 | Moon et al. |
| 2017/0113046 | A1 | 4/2017 | Fried et al. |
| 2017/0224908 | A1 | 8/2017 | Grasso et al. |
| 2017/0224980 | A1 | 8/2017 | Grasso et al. |
| 2017/0235663 | A1 | 8/2017 | Kattepur et al. |
| 2017/0246452 | A1 | 8/2017 | Liu et al. |
| 2017/0259072 | A1 | 9/2017 | Newham et al. |
| 2018/0078767 | A1 | 3/2018 | Rapoport et al. |
| 2018/0236221 | A1 | 8/2018 | Opie et al. |
| 2018/0332009 | A1 | 11/2018 | Lange |
| 2019/0110754 | A1 | 4/2019 | Rao et al. |
| 2019/0134396 | A1* | 5/2019 | Toth ........................ A43B 3/34 |
| 2019/0150774 | A1 | 5/2019 | Brinkmann et al. |
| 2019/0282817 | A1 | 9/2019 | Muller et al. |
| 2019/0333505 | A1 | 10/2019 | Stavisky et al. |
| 2020/0061374 | A1 | 2/2020 | Mitchell |
| 2020/0069427 | A1 | 3/2020 | Swennen et al. |
| 2020/0078586 | A1 | 3/2020 | Wijseundara et al. |
| 2020/0155828 | A1 | 5/2020 | Shepard et al. |
| 2020/0206503 | A1 | 7/2020 | Ganzer et al. |
| 2020/0215318 | A1 | 7/2020 | Fielder et al. |
| 2020/0222010 | A1 | 7/2020 | Howard |
| 2020/0310442 | A1 | 10/2020 | Halder et al. |
| 2020/0337579 | A1 | 10/2020 | Auerbach et al. |
| 2020/0364539 | A1 | 11/2020 | Ansimov et al. |
| 2021/0033559 | A1 | 2/2021 | Panat et al. |
| 2021/0034906 | A1 | 2/2021 | Van Welzen et al. |
| 2021/0085988 | A1 | 3/2021 | Nin et al. |
| 2021/0186450 | A1 | 6/2021 | Vancamberg et al. |
| 2021/0213279 | A1 | 7/2021 | Rapoport et al. |
| 2021/0252289 | A1 | 8/2021 | Esteller |
| 2021/0267523 | A1 | 9/2021 | Donoghue et al. |
| 2021/0267526 | A1 | 9/2021 | Donoghue et al. |
| 2021/0268265 | A1 | 9/2021 | Eder et al. |
| 2021/0272687 | A1 | 9/2021 | Klopfenstein et al. |
| 2021/0275807 | A1 | 9/2021 | Bouton |
| 2021/0280309 | A1 | 9/2021 | Klopfenstein et al. |
| 2021/0353439 | A1 | 11/2021 | Norman et al. |
| 2022/0005465 | A1 | 1/2022 | Prabhavalkar et al. |
| 2022/0117511 | A1 | 4/2022 | Shor et al. |
| 2022/0175320 | A1 | 6/2022 | Shah et al. |
| 2022/0184403 | A1 | 6/2022 | Chouinard et al. |
| 2022/0208173 | A1 | 6/2022 | Chang et al. |
| 2022/0211312 | A1 | 7/2022 | Brinkmann et al. |
| 2022/0218264 | A1 | 7/2022 | Brunner et al. |
| 2022/0240833 | A1 | 8/2022 | Oxley |
| 2022/0301563 | A1 | 9/2022 | Chang et al. |
| 2022/0370805 | A1 | 11/2022 | Cogan et al. |
| 2022/0379117 | A1 | 12/2022 | Spector |
| 2022/0413612 | A1 | 12/2022 | Gribetz |
| 2023/0059718 | A1 | 2/2023 | Hor-Lao et al. |
| 2023/0062326 | A1 | 3/2023 | Colachis et al. |
| 2023/0111217 | A1 | 4/2023 | Weiss |
| 2023/0113727 | A1 | 4/2023 | Van Der Zalm et al. |
| 2023/0210427 | A1 | 7/2023 | Rapoport et al. |
| 2023/0253104 | A1 | 8/2023 | Serruya et al. |
| 2023/0271007 | A1 | 8/2023 | Ganzer et al. |
| 2023/0320417 | A1 | 10/2023 | Renner et al. |
| 2023/0389851 | A1 | 12/2023 | Tal et al. |
| 2023/0414947 | A1 | 12/2023 | Esteller |
| 2024/0029717 | A1 | 1/2024 | Jain et al. |
| 2024/0115178 | A1 | 4/2024 | Rapoport |
| 2024/0139512 | A1 | 5/2024 | Schulhauser et al. |
| 2024/0374893 | A1 | 11/2024 | Robinson et al. |
| 2024/0399152 | A1 | 12/2024 | Powell et al. |
| 2024/0412030 | A1 | 12/2024 | Guinn et al. |
| 2025/0010070 | A1 | 1/2025 | Ganzer et al. |

FOREIGN PATENT DOCUMENTS

| | | | |
|---|---|---|---|
| CN | 110876652 | A | 3/2020 |
| KR | 20200074951 | A | 6/2020 |
| WO | 2008052166 | A2 | 5/2008 |
| WO | 2012143850 | A1 | 10/2012 |
| WO | 2015191628 | A1 | 12/2015 |
| WO | 2015195553 | A1 | 12/2015 |
| WO | 2017160627 | A2 | 9/2017 |
| WO | 2017196971 | A1 | 11/2017 |
| WO | 2019079475 | A1 | 4/2019 |
| WO | 2019152648 | A1 | 8/2019 |
| WO | 2019211314 | A1 | 11/2019 |
| WO | 2020008016 | A1 | 1/2020 |
| WO | 2020008017 | A1 | 1/2020 |
| WO | 2020142384 | A1 | 7/2020 |
| WO | 2020219371 | A1 | 10/2020 |
| WO | 2021021714 | A1 | 2/2021 |
| WO | 2021055682 | A1 | 3/2021 |
| WO | 2021162795 | A1 | 8/2021 |
| WO | 2021174061 | A1 | 9/2021 |
| WO | 2022011260 | A1 | 1/2022 |

(56) References Cited

FOREIGN PATENT DOCUMENTS

| | | | |
|---|---|---|---|
| WO | 2022126059 | A1 | 6/2022 |
| WO | 2022251151 | A1 | 12/2022 |
| WO | 2024254360 | A1 | 12/2024 |

OTHER PUBLICATIONS

International Preliminary Report on Patentability for the Application No. PCT/US2022/82619, mailed on Jul. 11, 2024, 9 pages.
International Preliminary Report on Patentability for the Application No. PCT/US2023/063894, mailed Sep. 19, 2024, 12 pages.
International Search Report and Written Opinion for Application No. PCT/US2024/017647, mailed on Jun. 6, 2024, 13 pages.
International Search Report and Written Opinion for Application No. PCT/US2024/028423, mailed on Jul. 18, 2024, 13 pages.
Kim T., et al., "Spatiotemporal Compression for Efficient Storage and Transmission of High-Resolution Electrocorticography Data," Annual International Conference of the IEEE Engineering in Medicine and Biology Society, Aug. 28, 2012, pp. 1012-1015.
Office Action for Canadian Patent Application No. 3241544, mailed Jul. 25, 2024, 3 pages.
Alim S.A., et al., "Some Commonly Used Speech Feature Extraction Algorithms," IntechOpen, 2018, vol. 1, 18 pages.
Anumanchipalli G.K., et al., "Speech Synthesis from Neural Decoding of Spoken Sentences," Nature, Apr. 2019, vol. 568, No. 7753, pp. 493-498.
Collobert R., et al., "A Fully Differentiable Beam Search Decoder," A preprint, Feb. 19, 2019, 11 pages.
Defossez A., et al., "Decoding Speech Perception from Non-invasive Brain Recordings," Nature Machine Intelligence, Oct. 5, 2023, vol. 5, pp. 1097-1107.
Duraivel S., et al., "High-resolution Neural Recordings Improve the Accuracy of Speech Decoding," Nature Communications, Nov. 6, 2023, vol. 14, No. 6938, 16 pages.
Haufe S., et al., "Elucidating Relations Between Fmri, Ecog and Eeg Through a Common Natural Stimulus," Publication bioR/iv. Oct. 22, 2017.
Inclusive Technology., "Inclusive Eyegaze Education with Mygaze Eye Tracker—Discontinued," Spectronics, Feb. 25, 2025, 8 pages, Retrieved from the Internet: URL: https://www.spectronics.com.au/product/inclusive-eyegaze-education-with-mygaze-eye-tracker#mygaze.
International Preliminary Report on Patentability for the Application No. PCT/US2023/035620, mailed May 1, 2025, 9 pages.
International Preliminary Report on Patentability for the Application No. PCT/US2023/035623, mailed May 1, 2025, 9 pages.
International Preliminary Report on Patentability for the Application No. PCT/US2023/035624, mailed May 1, 2025, 9 pages.
International Preliminary Report on Patentability for the Application No. PCT/US2023/035625, mailed May 1, 2025, 7 pages.
International Preliminary Report on Patentability for the Application No. PCT/US2023/035627, mailed May 1, 2025, 8 pages.
International Search Report and Written Opinion for Application No. PCT/US2025/011619, mailed on Mar. 27, 2025, 13 Pages.
Meta., "AI Speech Research Voicebox: Text-guided Multilingual Universal Speech Generation at Scale," Voicebox, Research by Meta AI, 2023, 8 pages, Retrieved on Feb. 25, 2025, Retrieved from the Internet: URL: https://voicebox.metademolab.com/.
International Preliminary Report on Patentability issued in International Application No. PCT/US2023/035620, 9 pages, dated May 1, 2025.
Chen et al., "Emerging Brain-to-Content Technologies From Generative AI and Deep Representation Learning (In the Spotlight)", IEEE Signal Processing Magazine, vol. 41, No. 6, pp. 94-104, Nov. 2024.
Biederman W., et al., "A Fully-Integrated, Miniaturized (0.125 $mm^2$) 10.5 μW Wireless Neural Sensor," IEEE Journal of Solid-state Circuits, 2013, vol. 48, No. 4, pp. 960-970.
Coelho K., et al., "Cryptographic Algorithms in Wearable Communications: An Empirical Analysis," IEEE Communications Letters, 2019, vol. 23, No. 11, pp. 1931-1934.
Examination Report No. 1 for Australian Patent Application No. 2023230897 dated Jun. 26, 2025, 10 pages.
Ghoreishizadeh S.S., et al., "A Lightweight Cryptographic System for Implantable Biosensors," Proceedings of 2014 IEEE Biomedical Circuits and Systems Conference (BioCAS), 2014, pp. 472-475.
Hinterberger T., et al., "Voluntary Brain Regulation and Communication with Electrocorticogram Signals," Epilepsy and Behavior, Aug. 1, 2008, vol. 13, No. 2, pp. 300-306.
International Search Report and Written Opinion for Application No. PCT/US2025/019165, mailed on Jun. 6, 2025, 18 pages.
Kim H., et al., "A Configurable and Low-Power Mixed Signal SoC for Portable ECG Monitoring Applications," IEEE Transactions on Biomedical Circuits and Systems, 2014, vol. 8, No. 2, pp. 257-267.
Schwemmer M.A., et al., "Meeting Brain-Computer Interface User Performance Expectations Using a Deep Neural Network Decoding Framework," Nature Medicine, Sep. 24, 2018, vol. 24, No. 11, pp. 1669-1676.
Yanagisawa T., et al., "Electrocorticographic Control of a Prosthetic Arm in Paralyzed Patients," Annals of Neurology, 2012, vol. 71, No. 3, pp. 353-361.
International Search Report and Written Opinion of the International Searching Authority issued in International Application No. PCT/US2023/035624, 15 pages, dated Feb. 26, 2024.
International Search Report and Written Opinion of the International Searching Authority issued in International Application No. PCT/US2022/082619, 16 pages, dated Jun. 2, 2023.
International Search Report and Written Opinion of the International Searching Authority issued in International Application No. PCT/US2023/035627, 13 pages, dated Feb. 9, 2024.
International Search Report and Written Opinion of the International Searching Authority issued in International Application No. PCT/US2023/035625, 13 pages, dated Feb. 26, 2024.
International Search Report and Written Opinion of the International Searching Authority issued in International Application No. PCT/US2023/035620, 14 pages, dated Feb. 15, 2024.
International Search Report and Written Opinion of the International Searching Authority issued in International Application No. PCT/US2022/078130, 11 pages, dated Feb. 16, 2023.
International Search Report and Written Opinion of the International Searching Authority issued in International Application No. PCT/US2023/063894, 14 pages, dated Sep. 29, 2023.
International Search Report and Written Opinion of the International Searching Authority issued in International Application No. PCT/US2023/035623, 10 pages, dated Feb. 8, 2024.
Camara et al, "Security and Privacy Issues in Implantable Medical Devices: A Comprehensive Survey", Journal of Biomedical Informatics, vol. 55, 45 pages, Jun. 11, 2015.
Hettick et al, "The Layer 7 Cortical Interface: A Scalable and Minimally Invasive Brain-Computer Interface Program". bioRxiv, 42 pages, Jan. 30, 2024.
Liu et al, "An Energy-Efficient Compressed Sensing-Based Encryption Scheme for Wireless Neural Recording, " IEEE Journal on Emerging Topic in Circuits and Systems, 10 pages, Jun. 2021.
Wang et al, "Unsupervised Decoding of Long-Term, Naturalistic Human Neural Recordings with Automated Video and Audio Annotations", frontiers in Human Neuroscience, vol. 10, Article 165, 13 pages, Apr. 21, 2016.
Sorrell et al, "Brain-Machine Interfaces: Closed-Loop Control in an Adaptive System", Annual Review of Control, Robotics, and Autonomous Systems, vol. 4, pp. 167-189, Jan. 29, 2021.
International Search Report and Written Opinion of the International Searching Authority issued in International Application No. PCT/US2023/077626, 12 pages, dated Feb. 28, 2024.
Beck C., et al., "Block Cipher Based Security for Severely Resource-Constrained Implantable Medical Devices," In Proceedings of the 4th International Symposium on Applied Sciences in Biomedical and Communication Technologies (ISABEL '11) Association for Computing Machinery, Oct. 26, 2011, No. 62, pp. 1-5.

(56) References Cited

OTHER PUBLICATIONS

Bridges D.C., et al., "MEA Viewer: A High-performance Interactive Application for Visualizing Electrophysiological Data," PLoS One, Feb. 9, 2018, vol. 12, No. 2, 10 pages.
Daemen J., et al., "AES Proposal: Rijndael," National Institute of Standards and Technology, 1999, 47 pages.
Judy M., et al., "A Nonlinear Signal-Specific ADC for Efficient Neural Recording," Biomedical Circuits and Systems Conference (BioCAS), 2010, pp. 17-20.
Kester Q.A., "A Cryptographic Image Encryption Technique for Facial-Blurring of Images," International Journal of Advanced Technology & Engineering Research, May 2013, vol. 3, No. 3, pp. 1-7.
Maji S., et al., "A Low-power Dual-Factor Authentication Unit for Secure Implantable Devices" IEEE Custom Integrated Circuits Conference (CICC), 2020, 10 pages, Retrieved from the Internet URL: https://arxiv.org/pdf/2004.13709.
Matsushita K., et al., "A Fully Implantable Wireless ECoG 128-Channel Recording Device for Human Brain-machine Interfaces: W-HERBS," Frontiers in Neuroscience, Jul. 30, 2018, vol. 12, No. 511, 11 pages.
Ogawa H., et al., "Rapid and Minimum Invasive Functional Brain Mapping by Real-time Visualization of High Gamma Activity During Awake Craniotomy," World Neurosurgery, Nov. 2014, 10 pages.
Pallud J., et al., Direct Electrical Bipolar Electrostimulation for Functional Cortical and Subcortical Cerebral Mapping in Awake Craniotomy. Practical Considerations, Neurochirurgie, Jun. 1, 2017, vol. 63, pp. 164-174.
Schneier B., "Description of a New Variable-Length Key, 64-Bit Block Cipher (Blowfish)," Fast Software Encryption, Cambridge Security Workshop Proceedings, Dec. 1993, pp. 191-204.
Tchoe Y., et al., "Human Brain Mapping with Multi-thousand Channel PtNRGrids Resolves Spatiotemporal Dynamics," Science Translational Medicine, Jan. 19, 2022, vol. 14, No. 628, 22 pages.
Third Party Prior Art Submission for U.S. Appl. No. 18/180,248, filed Aug. 12, 2025.
Thorpe C., et al., "A Coprime Blur Scheme for Data Security in Video Surveillance," In IEEE Transactions on Pattern Analysis and Machine Intelligence, 2013, vol. 35, No. 12, pp. 3066-3072.
Uy J., et al., "Stability of Maps of Human Motor Cortex Made with Transcranial Magnetic Stimulation," Brain Topography, Jun. 2002, vol. 14, No. 4, pp. 293-297.
International Search Report and Written Opinion of the International Searching Authority issued in International Application No. PCT/US2024/043449, 16 pages, dated Nov. 15, 2024.
Escabi M.A., et al., "A high-density, high-channel count, multiplexed muECoG array for auditory-cortex recordings" Journal of Neurophysiology, 2014, vol. 112, No. 6, pp. 1566-1583.
Office Action for Canadian Patent Application No. 3,245,576, mailed Oct. 14, 2025, 5 pages.
Rohaut B., et al., "Uncovering Consciousness in Unresponsive ICU Patients: Technical, Medical and Ethical Considerations," Critical Care, Mar. 9, 2019, vol. 23, No. 78, 9 pages, doi: 10.1186/s13054-019-2370-4.
"What are polymides?", UBE Corporation, accessed on Sep. 19, 2025, accessed at https://www.ube.com/ube/en/contents/chemical/ploymide/ploymide_column.html (Year: 2025).
Office Action for Canadian Patent Application No. 3,269,407, mailed Mar. 6, 2026 , 5 pages.

* cited by examiner

SECURE INTERFACES FOR NEURAL DEVICES

PRIORITY

The present application claims priority to U.S. Provisional Patent Application No. 63/417,837, titled SECURE INTERFACES FOR NEURAL DEVICES, filed Oct. 20, 2022, which is hereby incorporated by reference herein in its entirety.

BACKGROUND

Brain-computer interfaces have shown promise as systems for restoring, replacing, and augmenting lost or impaired neurological function in a variety of contexts, including paralysis from stroke and spinal cord injury, blindness, and some forms of cognitive impairment. Multiple innovations over the past several decades have contributed to the potential of these neural interfaces, including advances in the areas of applied neuroscience and multichannel electrophysiology, mathematical and computational approaches to neural decoding, power-efficient custom electronics and the development of application-specific integrated circuits, as well as materials science and device packaging. Nevertheless, the practical impact of such systems remains limited, with only a small number of patients worldwide having received highly customized interfaces through clinical trials.

Neural interfaces, which exchange data between the brain and devices outside the body, require unique and extraordinarily rigorous levels of security in order to ensure the integrity of the data they handle and the interactions they enable. These interfaces record, process, and transmit highly personal and sensitive data relating to the brain activity and thought processes of a user. This type of personal data has the potential to be uniquely sensitive, and therefore the measures put in place to secure such data are of even greater concern than those associated with other devices, implantable or otherwise, that handle personal or medical data.

Although the security of digital communications, including those related to personal electronic devices, has been the subject of substantial technological development over decades, the same standards of security have not historically been applied to implantable medical devices. The state-of-the-art for implantable electronic medical devices, even those which have communication interfaces for interacting with systems outside the body, includes no security or minimal security protocols at the device and system levels. The United States FDA and other regulatory agencies have not required security of this nature, even though substantial attention has been paid to the need to protect personal health data (as exemplified by HIPAA in the United States) and personal digital data (as exemplified by the GDPR in the European Union). With the advent of neural interface technologies comes a new imperative to secure data in digital interactions relating to implantable devices in general and neural interfaces in particular.

Neural interfaces have the potential to enable bidirectional communication between the brain of the user and systems external to the body. Complete security requires end-to-end protection of the data handled by such interfaces, and the processes through which the data is handled. As background, it is helpful to consider steps through which neural data is handled in a prototypical neural interface, with a view toward security at every stage and in the transitions between stages.

SUMMARY

The present disclosure is directed to data encryption systems for neural interfaces.

In one embodiment, there is provided a neural device system for use with a subject, the neural device system comprising: a neural device configured to sense data associated with the subject or receive control input, the neural device comprising: an electrode array configured to stimulate or record from neural tissue with which the electrode array is engaged, and one or more electronics modules; an external device communicably coupled to the neural device, the external device configured to at least one of receive or communicate data to the neural device; a storage medium communicably coupled to the receiver, the storage medium comprising data configured to be retrieved by the external device; and one or more communications interfaces between the neural device, the external device, and the storage medium or components thereof, wherein the one or more communications interfaces comprise an encryption protocol.

In some embodiments, the electrode array comprises penetrating electrodes.

In some embodiments, the electrode array comprises a nonpenetrating electrodes.

In some embodiments, the external device comprises a tablet, a smartphone, a laptop, a desktop, a secure server, a smartwatch, a head-mounted virtual reality device, a head-mounted augmented reality device, or a smart inductive charger device.

In some embodiments, all of the one or more communications interfaces are encrypted.

In some embodiments, a subset of the one or more communications interfaces are encrypted.

In some embodiments, the encryption protocol comprises at least one of Advanced Encryption Standard, Data Encryption Standard or variations thereof, Rivest-Shamir-Adleman, Blowfish, Twofish, successive approximation register architecture, bit stream cipher, or block stream cipher.

In some embodiments, at least one of the communications interfaces comprises a wired connection.

In some embodiments, at least one of the communications interfaces comprises a wireless connection.

In some embodiments, the one or more electronics modules comprise one or more of an electrode amplifier, an analog front-end stage, an analog-digital converter, a digital signal processor, or a transceiver.

FIGURES

DETAILED DESCRIPTION

The present disclosure is directed to secure communications interfaces for neural device systems, particularly communications interfaces implementing end-to-end encryption.

Neural Device Systems

Figure 1:
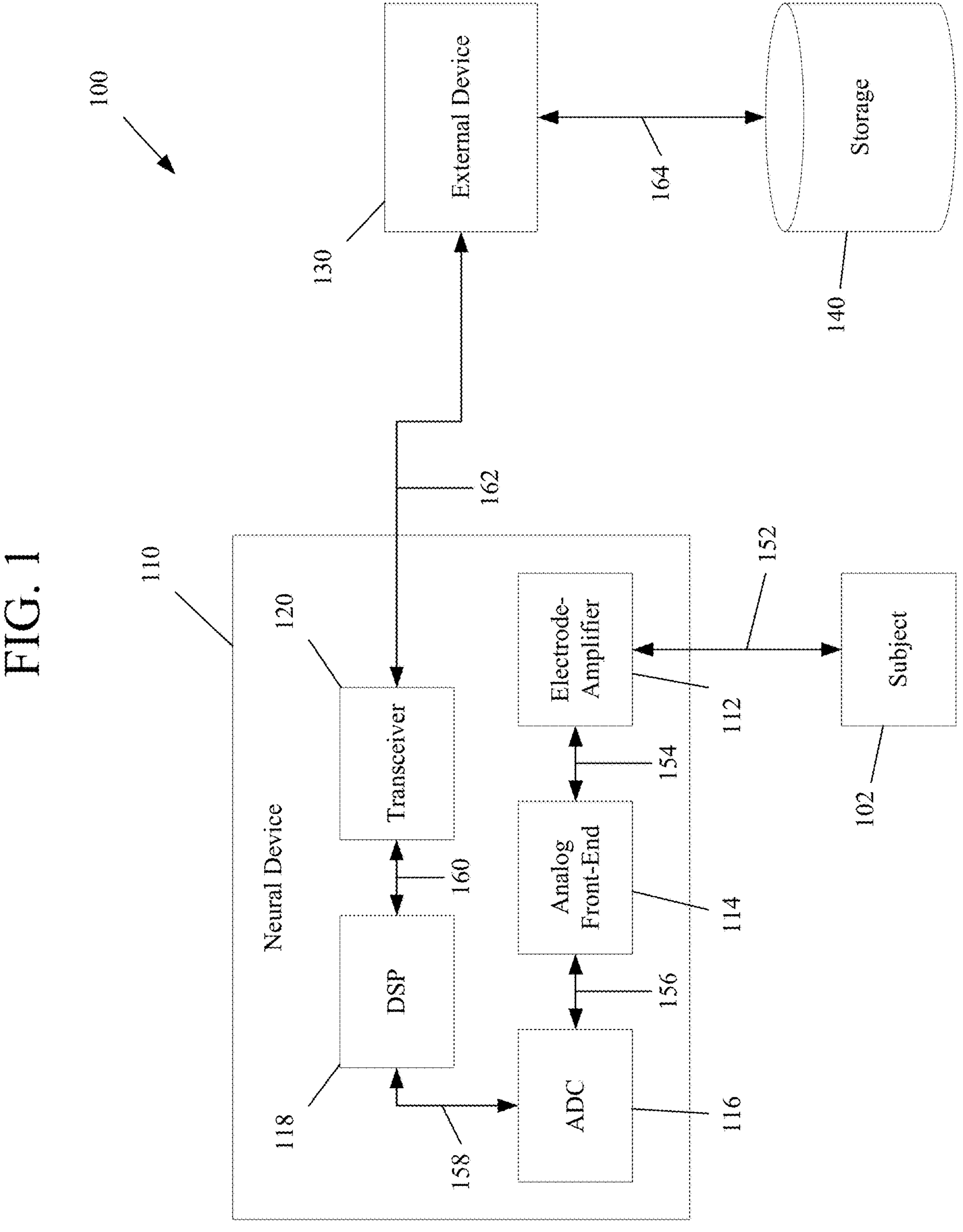
FIG. 1 illustrates a block diagram of a secure neural device data transfer system, in accordance with an embodiment of the present disclosure.

Neural devices can include electrode arrays that interface with a subject's brain in order to sense and/or stimulate the brain. In one embodiment, the neural devices can include penetrating electrodes, i.e., electrodes that penetrate the neural tissue and/or cortical surface. In another embodiment, the neural devices can include non-penetrating electrodes, i.e., electrodes that do not penetrate the neural tissue and/or cortical surface. Neural devices can sense and record brain activity, receive instructions for stimulating the subject's brain, and otherwise interact with a subject's brain as generally described herein. Accordingly, neural devices necessarily involve the use of communications interfaces in order to transfer data between the devices of the system and/or components thereof. Referring now to FIG. 1, there is shown a diagram of an illustrative system 100 including a neural device 110 that is communicatively coupled to an external device 130. The external device 130 can include any device that the neural device 110 can be communicatively coupled, such as a computer system or mobile device (e.g., a tablet, a smartphone, a laptop, a desktop, a secure server, a smartwatch, a head-mounted virtual reality device, a head-mounted augmented reality device, or a smart inductive charger device). In some embodiments, the external device 130 can further include or be communicatively coupled to storage 140. In one embodiment, the storage 140 could include a database stored on the external device 130. In another embodiment, the storage 140 can include a cloud computing system (e.g., Amazon Web Services or Azure).

The neural device 110 can include a range of electrical or electronic components. In the illustrated embodiment, the neural device 110 includes an electrode-amplifier stage 112, an analog front-end stage 114, an analog-to-digital converter (ADC) stage 116, a digital signal processing (DSP) stage 118, and a transceiver stage 120 that are communicatively coupled together. The electrode-amplifier stage 112 can include an electrode array, such as is described below, that is able to physically interface with the brain of the subject 102 in order to sense brain signals and/or apply electrical signals thereto. The analog front-end stage 114 can be configured to amplify signals that are sensed from or applied to the subject 102, perform conditioning of the sensed or applied analog signals, perform analog filtering, and so on. The front-end stage 114 can include, for example, one or more application-specific integrated circuits (ASICs) or other electronics. The ADC stage 116 can be configured to convert received analog signals to digital signals. The DSP stage 118 can be configured to perform various DSP techniques, including multiplexing of digital signals received via the electrode-amplifier stage 112 and/or from the external device 130. For example, the DSP stage 118 can be configured to convert instructions from the external device 130 to a corresponding digital signal. The transceiver stage 120 can be configured to transfer data from the neural device 110 to the external device 130 located outside of the body of the subject 102.

In various embodiments, the stages of the neural device 110 could provide unidirectional or bidirectional communications (as indicated in FIG. 1) by and between the neural device 110 and the external device 130. In various embodiments, one or more of the stages could operate in a serial or parallel manner with other stages of the system 100. It could further be noted that the depicted architecture for the system 100 is simply intended for illustrative purposes and that the system 100 could be arranged differently (i.e., components or stages could be connected in different manners) or include additional components or stages.

Figure 2:
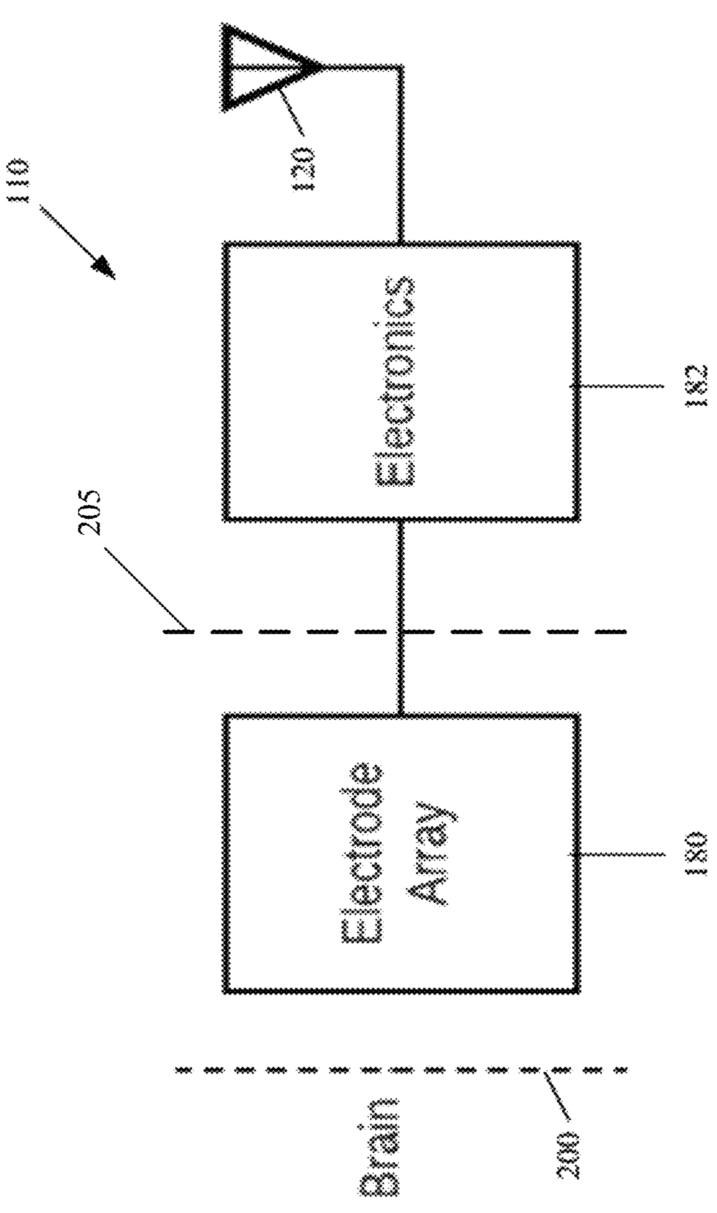
FIG. 2 illustrates a diagram of a neural device, in accordance with an embodiment of the present disclosure.

In some embodiments, the neural device 110 described above could include a brain implant, such as is shown in FIG. 2. The neural device 110 may be a biomedical device configured to study, investigate, diagnose, treat, and/or augment brain activity. In some embodiments, the neural device 110 may be a subdural neural device, i.e., a neural device implanted between the dura 205 (i.e., the membrane surrounding the brain) and the cortical surface of the brain 200. In some embodiments, the neural device 110 may be positioned beneath the dura mater 205 or between the dura mater 205 and the arachnoid membrane. In some embodiments, the neural device 110 may be positioned in the subdural space, on the cortical surface of the brain 200. The neural device 110 may be inserted through an incision in the scalp 202 and across the dura 205. The neural device 110 can include an electrode array 180 (which may be a component of or coupled to the electrode-amplifier stage 112 described above) that is configured to record and/or stimulate an area of the brain 200. The electrode array 180 can be connected to an electronics hub 182 (which could include one or more of the electrode-amplifier stage 112, analog front-end stage 114, ADC stage 116, and DSP stage 118) that is configured to transmit via wireless or wired transceiver 120 to the external device 120 (in some cases, referred to as a "receiver").

The electrode array 180 can comprise non-penetrating cortical surface microelectrodes (i.e., the electrode array 180 does not penetrate the brain 200). Accordingly, the neural device 110 could provide a high spatial-resolution, with minimal invasiveness and improved signal quality. The minimal invasiveness of the electrode array 180 is beneficial because it allows the neural device 110 to be used with larger population of patients than conventional brain implants, thereby expanding the application of the neural device 110 and allowing more individuals to benefit from brain-computer interface technologies. Furthermore, the surgical procedures for implanting the neural devices 110 are minimally invasive, reversible, and avoid damaging neural tissue. In some embodiments, the electrode array 180 can be a high-density microelectrode array that provides smaller features and improved spatial resolution relative to conventional neural implants.

In some embodiments, the neural device 110 includes an electrode array configured to stimulate or record from neural tissue adjacent to the electrode array, and an integrated circuit in electrical communication with the electrode array, the integrated circuit having an analog-to-digital converter (ADC) producing digitized electrical signal output. In some embodiments, the ADC or other electronic components of the neural device 110 can include an encryption module, such as is described below. The neural device 110 can also include a wireless transmitter (e.g., the transceiver 120) communicatively coupled to the integrated circuit or the encryption module and an external device 130. The neural device 110 can also include, for example, control logic for operating the integrated circuit or electrode array 180, memory for storing recordings from the electrode array, and a power management unit for providing power to the integrated circuit or electrode array 180.

Additional information regarding brain-computer interfaces described herein can be found in Ho et al., *The Layer 7 Cortical Interface: A Scalable and Minimally Invasive Brain-Computer Interface Platform*, bioRxiv 2022.01.02.474656; doi: https://doi.org/10.1101/2022.01.02.474656, which is hereby incorporated by reference herein in its entirety.

Secure Communications Systems for Neural Devices

As generally noted above, data security is critical for neural interfaces, such as the system 100 described above. Further, different inputs can be possible at each stage and each stage can be programmed or tampered with in a variety of different manners. Therefore, communications security for such systems 100 is important to ensure the ultimate functionality and operability of the systems 100.

Referring back to FIG. 1, the system 100 can include one or more communications interfaces between the neural device 110, the external device 130, the storage 140, and/or components thereof. In the illustrated embodiment, the system 100 includes a biotic-abiotic interface 152, which is the interface between the subject 102 and the neural device 110. The biotic-abiotic interface 152 is the interface between the tissue and/or organ of the subject 102 and the neural device 110. The system 100 can further include a front end-amplifier interface 154, a front-end-ADC interface 156, an ADC-DSP interface 118, a DSP-transceiver interface 160, a neural device-external device interface 162 (through the transceiver stage 120), and an external device-storage interface 164. One or more of the interfaces 152, 154, 156, 158, 160, 162, 164 can be configured to implement or execute encryption protocols, algorithms, or techniques to encrypt signals or data transferred by and/or between the corresponding components of the system 100. In various embodiments, the interfaces 152, 154, 156, 158, 160, 162, 164 could include hardware and/or software encryption. In various embodiments, the interfaces 152, 154, 156, 158, 160, 162, 164 could include symmetric or asymmetric encryption. In various embodiments, the interfaces 152, 154, 156, 158, 160, 162, 164 could be configured to implement Advanced Encryption Standard (AES), Data Encryption Standard (DES) or variations thereof (e.g., Triple DES), Rivest-Shamir-Adleman (RSA), Blowfish, Twofish, successive approximation register (SAR) architecture, bit stream cipher, or block stream cipher, for example. Further, the interfaces 152, 154, 156, 158, 160, 162, 164 can include wired or wireless connections between the corresponding components of the system 100.

In some embodiments, the system 100 can be configured to implement an end-to-end encryption, i.e., all or substantially all of the interfaces described above could implement an encryption protocol or encryption techniques. In other embodiments, a subset of the stages or components of the system 100 described above could implement an encryption protocol or encryption techniques.

Additional information regarding techniques for implementing secure communications in neural device systems can be found in U.S. patent application Ser. No. 18/180,248, titled SYSTEMS AND METHODS FOR IN-BODY SECURITY EMPLOYING HARDWARE-LEVEL SYSTEMS IN BIDIRECTIONAL NEURAL INTERFACES, filed Mar. 8, 2023, which is hereby incorporated by reference herein in its entirety.

This disclosure is not limited to the particular systems, devices and methods described, as these may vary. The terminology used in the description is for the purpose of describing the particular versions or embodiments only, and is not intended to limit the scope of the disclosure.

The following terms shall have, for the purposes of this application, the respective meanings set forth below. Unless otherwise defined, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the term "implantable medical device" includes any device that is at least partially introduced, either surgically or medically, into the body of a subject and is intended to remain there after the procedure.

As used herein, the singular forms "a," "an," and "the" include plural references, unless the context clearly dictates otherwise. Thus, for example, reference to a "protein" is a reference to one or more proteins and equivalents thereof known to those skilled in the art, and so forth.

As used herein, the term "about" means plus or minus 10% of the numerical value of the number with which it is being used. Therefore, about 50 mm means in the range of 45 mm to 55 mm.

As used herein, the term "consists of" or "consisting of" means that the device or method includes only the elements, steps, or ingredients specifically recited in the particular claimed embodiment or claim.

In embodiments or claims where the term "comprising" is used as the transition phrase, such embodiments can also be envisioned with replacement of the term "comprising" with the terms "consisting of" or "consisting essentially of."

As used herein, the term "subject" as used herein includes, but is not limited to, humans and non-human vertebrates such as wild, domestic, and farm animals.

While the present disclosure has been illustrated by the description of exemplary embodiments thereof, and while the embodiments have been described in certain detail, it is not the intention of the Applicants to restrict or in any way limit the scope of the appended claims to such detail. Additional advantages and modifications will readily appear to those skilled in the art. Therefore, the disclosure in its broader aspects is not limited to any of the specific details, representative devices and methods, and/or illustrative examples shown and described. Accordingly, departures may be made from such details without departing from the spirit or scope of the Applicant's general inventive concept.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The invention claimed is:

1. A neural device system for use with a subject, the neural device system comprising:

- a neural device configured to sense data associated with the subject or receive control input, the neural device comprising:
  - an electrode array configured to stimulate or record from neural tissue with which the electrode array is engaged,
  - a plurality of electronics modules, and
  - a communications interface between two of the plurality of electronics modules, the communications interface comprising an encryption protocol;
- an external device communicably coupled to the neural device, the external device configured to at least one of receive or communicate data to the neural device; and
- a storage medium communicably coupled to the external device, the storage medium comprising data configured to be retrieved by the external device.

2. The neural device system of claim 1, wherein the electrode array comprises penetrating electrodes.

3. The neural device system of claim 1, wherein the electrode array comprises nonpenetrating electrodes.

4. The neural device system of claim 1, wherein the external device comprises a tablet, a smartphone, a laptop, a desktop, a secure server, a smartwatch, a head-mounted virtual reality device, a head-mounted augmented reality device, or a smart inductive charger device.

5. The neural device system of claim 1, wherein all of the one or more communications interfaces are encrypted.

6. The neural device system of claim 1, wherein a subset of the one or more communications interfaces are encrypted.

7. The neural device system of claim 1, wherein the encryption protocol comprises at least one of Advanced Encryption Standard, Data Encryption Standard or variations thereof, Rivest-Shamir-Adleman, Blowfish, Twofish, successive approximation register architecture, bit stream cipher, or block stream cipher.

8. The neural device system of claim 1, wherein at least one of the communications interfaces comprises a wired connection.

9. The neural device system of claim 1, wherein at least one of the communications interfaces comprises a wireless connection.

10. The neural device system of claim 1, wherein the one or more electronics modules comprise one or more of an electrode amplifier, an analog front-end stage, an analog-digital converter, a digital signal processor, or a transceiver.

* * * * *